United States Patent
Gerrish (12)

(10) Patent No.: US 6,358,503 B1
(45) Date of Patent: Mar. 19, 2002

(54) PROTECTANT FILM FOR SKIN

(75) Inventor: Donald Lee Gerrish, Mankato, MN (US)

(73) Assignee: Coloplast Corp., North Mankato, MN (US)

( * ) Notice: Subject to any disclaimer, the term of this patent is extended or adjusted under 35 U.S.C. 154(b) by 0 days.

(21) Appl. No.: 09/670,986

(22) Filed: Sep. 26, 2000

(51) Int. Cl.$^7$ .................. A61K 31/74; A61K 7/00; A61K 7/021
(52) U.S. Cl. .............. 424/78.03; 424/401; 424/63
(58) Field of Search ............... 424/78.03, 401, 424/63

(56) References Cited

U.S. PATENT DOCUMENTS 5,103,812 A * 4/1992 Salamone et al. ............ 602/52
6,083,516 A * 7/2000 Curtis et al. ................ 424/401

* cited by examiner

Primary Examiner—Thurman K. Page
Assistant Examiner—Blessing Fubara
(74) Attorney, Agent, or Firm—Oppenheimer Wolff & Donnelly LLP

(57) ABSTRACT

An improved skin-protecting film-forming composition uses the polymer cycloalkyl methacrylate copolymer. In general, a composition according to the present invention comprises: cycloalkyl methacrylate copolymer; an evaporative solvent comprising at least one solvent for the cycloalkyl methacrylate copolymer that can evaporate so that the copolymer is deposited on the skin; and a plasticizer to provide flexibility to the film deposited on the skin. The composition dries to produce a protective film for skin when applied to the skin of a user. A preferred composition according to the present invention comprises about 19 percent of cycloalkyl methacrylate copolymer, about 1 percent of acetyl tributyl citrate, about 30 percent of isooctane, and about 50 percent of hexamethyldisiloxane. Another composition according to the present invention comprises about 19 percent of cycloalkyl methacrylate copolymer, about 1 percent of acetyl tributyl citrate, about 19 percent of isooctane, about 11 percent of isododecane, and about 50 percent of hexamethyldisiloxane.

15 Claims, No Drawings

PROTECTANT FILM FOR SKIN

BACKGROUND OF THE INVENTION

This invention is directed to a composition that dries to produce a protective film for skin when applied to the skin of a user.

In many circumstances, it is desirable to apply a protectant film to the skin. Such film protectants are particularly desirable in circumstances in which a wound or opening is present for a long period of time and must be protected. Such protectants are particularly useful in connection with incontinence and ostomy appliances, such as are used after a colostomy. Such films should protect the skin against germs, feces, enzymatic drainage or wound drainage, as well as adhesive trauma. Additionally, such films should be flexible on the skin so that they will not crack or flake and should not interfere with adhesion of ostomy appliances, wound care dressing, tape, or attachable breast forms. Moreover, such films should leave a shiny appearance so that one can see that the film has been applied, and should not leave a residue or irritate the skin.

Although a number of films for such uses currently exist, there is a need for films with improved properties that meet the exacting demands of use, particularly in the case of ostomy apertures. There is therefore a need for skin-protecting film-forming polymers with improved properties.

SUMMARY

A composition according to the present invention that dries to produce a protective film for skin when applied to the skin of a user comprises:

(1) cycloalkyl methacrylate copolymer;
(2) an evaporative solvent comprising at least one solvent for the cycloalkyl methacrylate copolymer that can evaporate so that the copolymer is deposited on the skin; and
(3) a plasticizer to provide flexibility to the film deposited on the skin.

A preferred cycloalkyl methacrylate copolymer is a bicycloalkyl methacrylate copolymer.

Typically, the solvent system comprises hexamethyldisiloxane and at least one saturated branched-chain hydrocarbon selected from the group consisting of isooctane, isodecane, and isododecane. Preferably, the saturated branched-chain hydrocarbon is isooctane. Alternatively, the saturated branched-chain hydrocarbon can be a mixture of isooctane and isododecane.

Typically, the plasticizer is selected from the group consisting of acetyl tributyl citrate, acetyl triethyl citrate, tributyl citrate, triethyl citrate, acetyl tripropyl citrate, tripropyl citrate, dibutyl sebacate, acetyl dibutyl sebacate, dipropyl sebacate, acetyl dipropyl sebacate, diethyl sebacate, and acetyl diethyl sebacate. Preferably, the plasticizer is acetyl tributyl citrate.

Preferably, the composition comprises from about 5 percent to about 25 percent of the cycloalkyl methacrylate copolymer, from about 73 percent to about 94.5 percent of the evaporative solvent, and from about 0.5 percent to about 2.0 percent of the plasticizer.

Preferably, when the evaporative solvent comprises isooctane and hexamethyldisiloxane, the ratio of isooctane to hexamethyldisiloxane is about 3:5. When the evaporative solvent comprises isooctane, isododecane, and hexamethyldisiloxane, the ratio of isooctane, isododecane, and hexamethyldisiloxane is preferably about 19:11:50.

In a particularly preferred embodiment, the composition comprises:

(1) about 19% cycloalkyl methacrylate copolymer;
(2) about 1% of acetyl tributyl citrate;
(3) about 30% of isooctane; and
(4) about 50% of hexamethyldisiloxane.

In an alternative embodiment, the composition comprises:

(1) about 19% cycloalkyl methacrylate copolymer;
(2) about 1% of acetyl tributyl citrate;
(3) about 19% of isooctane;
(4) about 11% of isododecane; and
(5) about 50% of hexamethyldisiloxane.

DESCRIPTION

An improved skin-protecting film-forming composition uses the polymer cycloalkyl methacrylate copolymer. This creates a unique protectant film when the polymer is dispersed in a solvent system that evaporates rapidly.

In general, a composition of the present invention is a composition that dries to produce a protectant film for skin when applied to the skin of a user. The composition comprises:

(1) cycloalkyl methacrylate copolymer;
(2) an evaporative solvent comprising at least one solvent for the cycloalkyl methacrylate copolymer that can evaporate so that the copolymer is deposited on the skin; and
(3) a plasticizer to provide flexibility to the film deposited on the skin.

A suitable source of a cycloalkyl methacrylate copolymer that is useful in compositions according to the present invention is Phoenix Chemical, Inc. of Somerville, N.J. A particularly suitable cycloalkyl methacrylate copolymer is a bicycloalkyl methacrylate copolymer marketed by Phoenix Chemical as Giovarez AC-5099M.

Typically, the solvent system comprises hexamethyldisiloxane and at least one saturated branched-chain hydrocarbon selected from the group consisting of isooctane, isodecane, and isododecane. Preferably, the saturated branched-chain hydrocarbon is a mixture of isooctane and isododecane. Alternatively, the saturated branched-chain hydrocarbon can be isooctane. Other saturated branched-chain hydrocarbons can be used.

Typically, the plasticizer is selected from the group consisting of acetyl tributyl citrate, acetyl triethyl citrate, tributyl citrate, triethyl citrate, acetyl tripropyl citrate, tripropyl citrate, dibutyl sebacate, acetyl dibutyl sebacate, dipropyl sebacate, acetyl dipropyl sebacate, diethyl sebacate, and acetyl diethyl sebacate. Preferably, the plasticizer is acetyl tributyl citrate. Other plasticizers can be used, including homologues and derivatives of these esters.

Preferably, the composition comprises from about 5% to about 25% of the cycloalkyl methacrylate copolymer, from about 73% to about 94.5% of the evaporative solvent, and from about 0.5% to about 2.0% of the plasticizer.

Where the evaporative solvent comprises isooctane and hexamethyldisiloxane, the ratio of isooctane to hexamethyldisiloxane is preferably about 3:5. When the evaporative solvent comprises isooctane, isododecane, and hexamethyldisiloxane, the ratio of isooctane, isododecane, and hexamethyldisiloxane is preferably about 19:11:50.

In a particularly preferred embodiment, the composition comprises:

(1) about 19% cycloalkyl methacrylate copolymer;

(2) about 1% of acetyl tributyl citrate;

(3) about 30% of isooctane; and (4) about 50% of hexamethyldisiloxane.

In an alternative embodiment, the composition comprises:

(1) about 19% cycloalkyl methacrylate copolymer;

(2) about 1% of acetyl tributyl citrate;

(3) about 19% of isooctane;

(4) about 11% of isododecane; and (5) about 50% of hexamethyldisiloxane.

The composition is made by adding the solvents (isooctane and/or isododecane and hexamethyldisiloxane) to the polymer and plasticizer and mixing with vigorous agitation.

The polymer is applied to the skin and forms a protective film that can be used, for example, to cover ostomy apertures, wounds, and other openings in the skin.

ADVANTAGES OF THE INVENTION

The present invention provides a protectant film that leaves a clear film on the skin. The skin is flexible on the skin so that it will not crack or flake. The film does not interfere with adhesion of ostomy appliances, wound care dressing, tape, or attachable breast forms. The film protects skin against urine, feces, enzymatic drainage, wound drainage or adhesive trauma. The application of the film leaves a shiny appearance so that one can see that the film has been applied.

The composition of the present invention is non-stinging. The solvent of the composition evaporates rapidly, leaving a dry film. These properties enhance the performance of the composition.

Although the present invention has been described in considerable detail, with reference to certain preferred versions thereof, other versions and embodiments are possible. Therefore, the scope of the invention is determined by the following claims.

I claim:

1. A composition that dries to produce a protective film for skin when applied to the skin of a user comprising:

(a) cycloalkyl methacrylate copolymer;

(b) an evaporative solvent system comprising hexamethyldisiloxane and at least one saturated branched-chain hydrocarbon selected from the group consisting of isooctane, isodecane, and isododecane that is a solvent for the cycloalkyl methacrylate copolymer and can evaporate so that the copolymer is deposited on the skin, the cycloalkyl methacrylate copolymer being soluble in the evaporative solvent system; and (c) a plasticizer to provide flexibility to the film deposited on the skin.

2. The composition of claim 1 wherein the at least one saturated branched-chain hydrocarbon is a mixture of isooctane and isododecane.

3. The composition of claim 1 wherein the at least one saturated branched-chain hydrocarbon is isooctane.

4. The composition of claim 1 wherein the plasticizer is selected from the group consisting of acetyl tributyl citrate, acetyl triethyl citrate, tributyl citrate, triethyl citrate, acetyl tripropyl citrate, tripropyl citrate, dibutyl sebacate, acetyl dibutyl sebacate, dipropyl sebacate, acetyl dipropyl sebacate, diethyl sebacate, and acetyl diethyl sebacate.

5. The composition of claim 4 wherein the plasticizer is acetyl tributyl citrate.

6. The composition of claim 1 wherein the cycloalkyl methacrylate copolymer is a bicycloalkyl methacrylate copolymer.

7. The composition of claim 1 wherein the composition comprises from about 5 percent to about 25 percent of the cycloalkyl methacrylate copolymer, from about 73 percent to about 94.5 percent of the evaporative solvent, and from about 0.5 percent to about 2.0 percent of the plasticizer.

8. The composition of claim 1 wherein the evaporative solvent comprises a mixture of isooctane and isododecane, and the plasticizer is acetyl tributyl citrate.

9. The composition of claim 1 wherein the evaporative solvent comprises isooctane and hexamethyldisiloxane, and the plasticizer is acetyl tributyl citrate.

10. The composition of claim 8 wherein the composition comprises from about 5 percent to about 25 percent of the cycloalkyl methacrylate copolymer, from about 73 percent to about 94.5 percent of the evaporative solvent, and from about 0.5 percent to about 2.0 percent of the plasticizer.

11. The composition of claim 9 wherein the composition comprises from about 5 percent to about 25 percent of the cycloalkyl methacrylate copolymer, from about 73 percent to about 94.5 percent of the evaporative solvent, and from about 0.5 percent to about 2.0 percent of the plasticizer.

12. The composition of claim 8 wherein the ratio of isooctane, isododecane, and hexamethyldisiloxane is about 19:11:50.

13. The composition of claim 9 wherein the ratio of isooctane to hexamethyldisiloxane is about 3:5.

14. A composition that dries to produce a protective film for skin when applied to the skin of a user comprising:

(a) about 19 percent of cycloalkyl methacrylate copolymer;

(b) about 1 percent of acetyl tributyl citrate;

(c) about 30 percent of isooctane; and (d) about 50 percent of hexamethyldisiloxane.

15. A composition that dries to produce a protective film for skin when applied to the skin of a user comprising:

(a) about 19 percent of cycloalkyl methacrylate copolymer;

(b) about 1 percent of acetyl tributyl citrate;

(c) about 19 percent of isooctane;

(d) about 11 percent of isododecane; and (e) about 50 percent of hexamethyldisiloxane.

* * * * *